United States Patent [19]
Task

[11] Patent Number: 5,557,403
[45] Date of Patent: Sep. 17, 1996

[54] SYSTEM AND METHOD FOR MEASURING CRAZING IN A TRANSPARENCY

[75] Inventor: Harry L. Task, Dayton, Ohio

[73] Assignee: The United States of America as represented by the Secretary of the Air Force, Washington, D.C.

[21] Appl. No.: 415,407

[22] Filed: Apr. 3, 1995

[51] Int. Cl.⁶ .................................................. G01N 21/00
[52] U.S. Cl. ...................... 356/239; 356/240; 356/124; 356/146
[58] Field of Search .................................. 356/239, 240, 356/237, 124, 446

[56] References Cited

U.S. PATENT DOCUMENTS 3,478,218  11/1969  Wuellner et al. ..................... 356/239
3,656,854  4/1972  Bricker ................................. 356/239

Primary Examiner—Frank Gonzalez
Assistant Examiner—Reginald A. Ratliff
Attorney, Agent, or Firm—Bobby D. Scearce; Thomas L. Kundert

[57] ABSTRACT

A system for measuring crazing in a transparency is described which comprises one or more light sources disposed near a first surface of the transparency for projecting light rays through the transparency at the portion thereof having a crazed condition, optical detectors corresponding in number to the number of light sources disposed on the opposite side of the transparency, each detector positioned to detect only light from a single corresponding source reflected from the crazed portion of the transparency, and a source of power for the sources and detectors. A sequencing circuit may be included to selectively activate selected light sources and corresponding optical detectors.

8 Claims, 2 Drawing Sheets

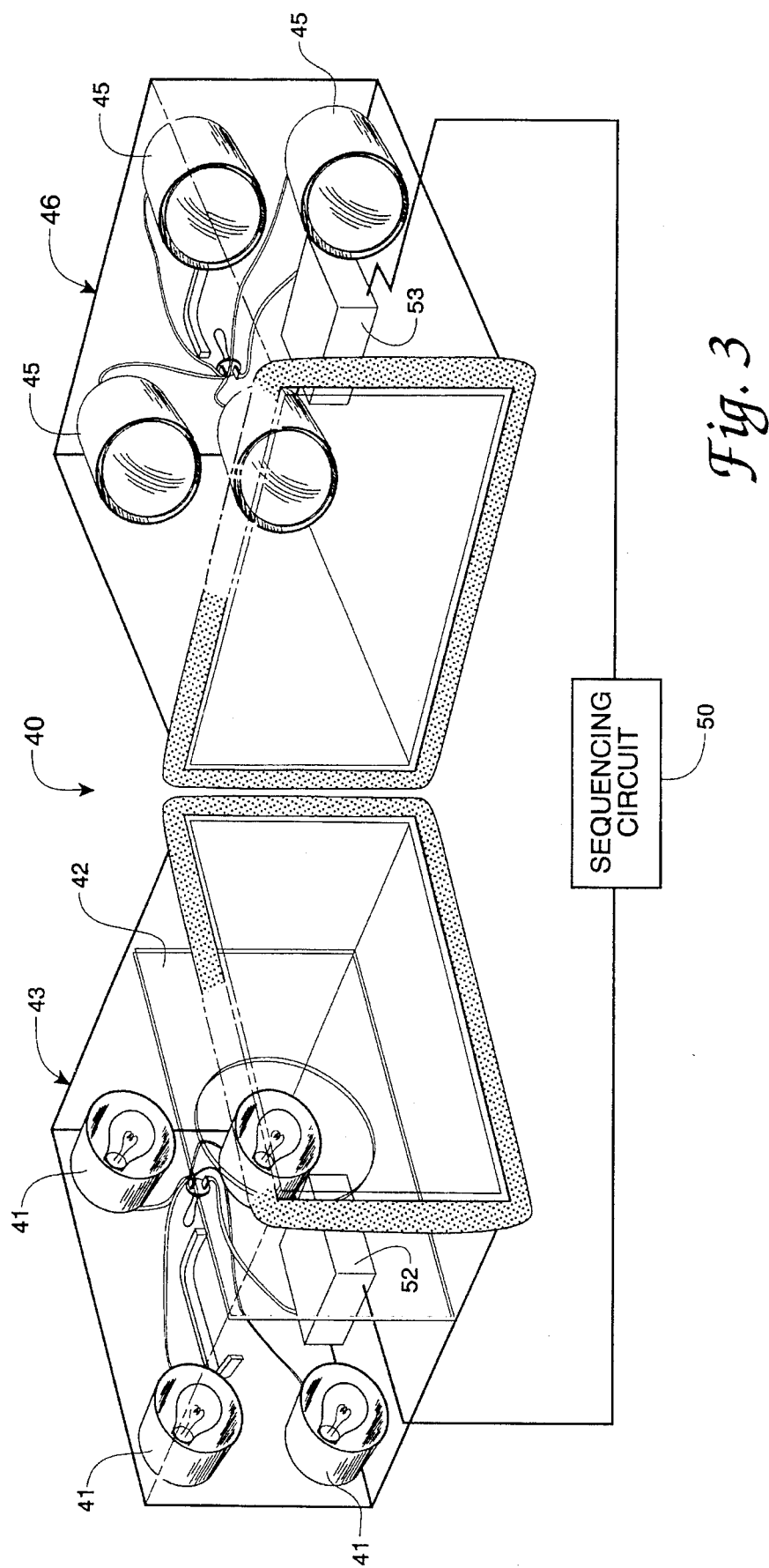

SYSTEM AND METHOD FOR MEASURING CRAZING IN A TRANSPARENCY

RIGHTS OF THE GOVERNMENT

The invention described herein may be manufactured and used by or for the Government of the United States for all governmental purposes without the payment of any royalty.

BACKGROUND OF THE INVENTION

The present invention relates to a system for quantifying the degree of crazing in plastic transparencies, such as those used for aircraft windscreens and passenger cabin windows.

Aircraft transparencies and commercial aircraft cabin windows tend to craze if subjected to mechanical or chemical stress. Crazing is the phenomena that results in tiny microcracks in a transparency surface. In general, the microcracks are perpendicular to the surface and are usually aligned in a structured pattern corresponding to the direction of applied stress. The microcracks are wide enough that the two sides of the crack are not in optical contact, and therefore behave like tiny mirrors and reflect light according to the law of reflection. The visual effect of crazing is that the transparency will suddenly illuminate if a light source (such as the sun) is in a correct position with respect to the eye position where the law of reflection is satisfied. If no light source is in the connect position with respect to the eye, the transparency may exhibit only a minor haze effect and may be otherwise substantially totally transparent. The crazing phenomena is therefore somewhat insidious in that it occurs only under certain conditions. No commercial system is available for quantitatively measuring the degree of crazing in transparencies with any acceptable degree of reliability, and it is highly desirable to have a system for quantifying crazing in aircraft transparencies for replacement when safe limits of crazing are exceeded.

The invention meets the need as just suggested by providing a system for quantitatively measuring crazing in plastic transparencies. The system of the invention includes a diffuse light source disposed on one side of the transparency and a calibrated photometric light detector on the other side arranged to capture and quantify the amount of light reflected from the microcracks comprising the crazed condition. The amount of reflected light is proportional to the degree (quantity and size of microcracks) of crazing in the transparency.

The invention can easily be configured as a portable system and facilitates a determination of the amount of crazing in an aircraft transparency without removing the transparency from the aircraft. The system is highly sensitive to the orientation of the microcracks.

The invention may find substantial use on aircraft to determine when crazing has reached a level requiring replacement of the transparency, for establishing limits on crazing for removal of critical passenger windows used by flight crews for inspecting the leading edge of wings for icing, and for setting basic FAA safety standards regarding crazing in commercial airline windows.

SUMMARY OF THE INVENTION

In accordance with the foregoing principles and objects of the invention, a system for measuring crazing in a transparency is described which comprises one or more light sources disposed near a first surface of the transparency for projecting fight rays through the transparency at the portion thereof having a crazed condition, optical detectors corresponding in number to the number of light sources disposed on the opposite side of the transparency, each detector positioned to detect only light from a single corresponding source reflected from the crazed portion of the transparency, and a source of power for the sources and detectors. A sequencing circuit may be included to selectively activate selected light sources and corresponding optical detectors.

DESCRIPTION OF THE DRAWINGS

The invention will be more clearly understood from the following detailed description of representative embodiments thereof read in conjunction with the accompanying drawings wherein:

FIG. 3 is a schematic perspective view in partial cutaway of an alternative embodiment of the invention.

DETAILED DESCRIPTION

Figure 2:
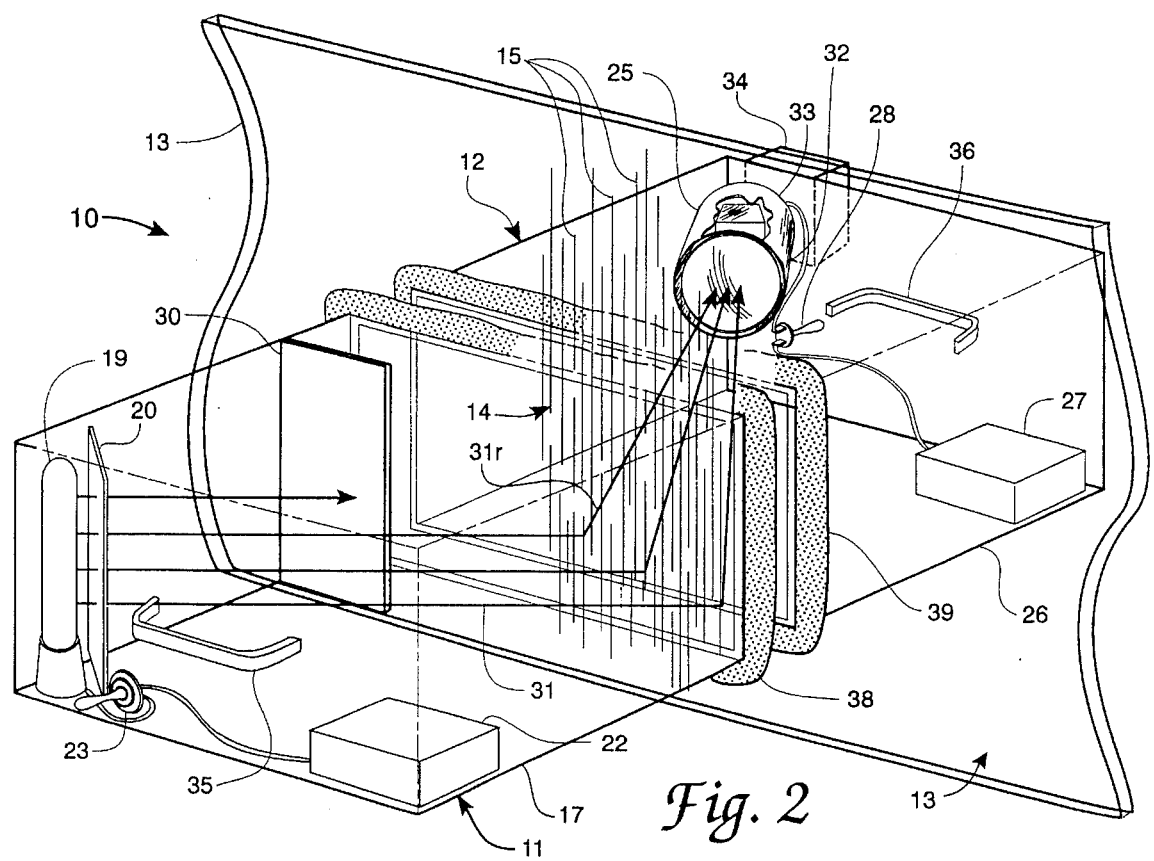
FIG. 2 is a schematic perspective view in partial cutaway of the FIG. 1 system.
Figure 1:
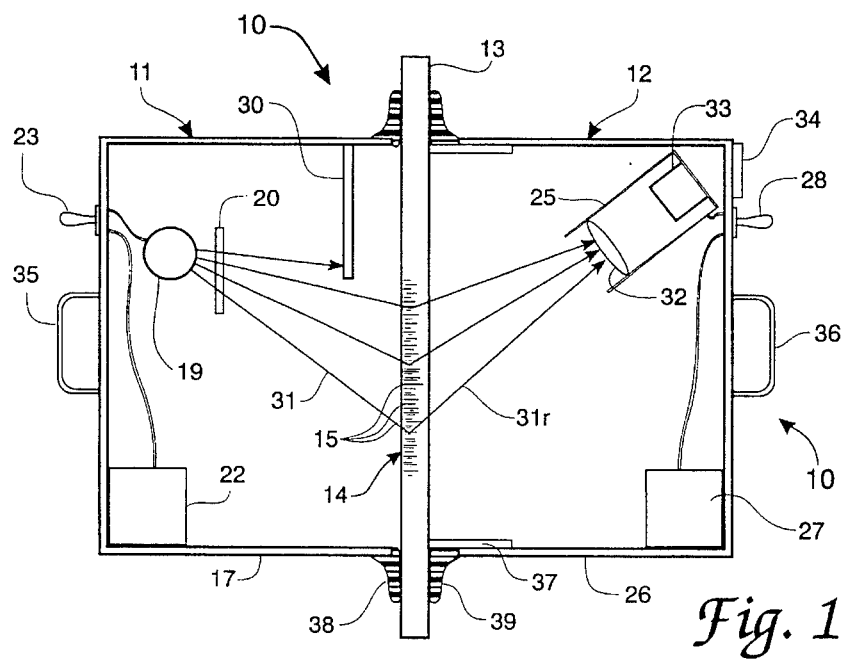
FIG. 1 is a schematic top view of the crazing measurement system of the invention.

Referring now to the drawings, FIG. 1 shows a schematic top view of the crazing measurement system of the invention. FIG. 2 shows a perspective view in partial cutaway of the system of FIG. 1. In accordance with a principle feature of the invention, representative system 10 may comprise a first light source portion 11 and a second detector portion 12 housed separately and configured for placement on opposite sides of a transparency 13 to be tested for the presence of crazing. Source portion 11 may be placed on either side of transparency 13 in order to effect a measurement, but, because of the geometry of the measurement system relative to transparency 13 being measured, it may be preferable to place source portion 11 on the side of transparency 13 having the suspected crazed condition (indicated generally at crazed region 14). The crazed condition of region 14 is characterized by tiny microcracks 15 in the transparency surface which behave like tiny mirrors.

Light source portion 11 comprises substantially light fight housing 17 enclosing a distributed light source 19. Light source 19 preferably comprises an elongated source having a large light emitting surface, such as might be provided by one or more elongated fluorescent lamps or an array of smaller fluorescent, incandescent, or other type of lamps, or any combination of lamps disposed behind optional diffuser 20. Light source 19 may be a point or line source, but preferably comprises an extended or distributed source in order to ensure that some part of source 19 satisfies the laws of reflection geometry with respect to the orientation of microcracks 15 and the location detector portion 12, and is preferably large enough, as by including a diffuser 20, to maximize the sensitivity of system 10 to multiple angles of microcracks 15. Light source 19 is powered by any suitable power source 22 as would occur to one practicing the invention, including AC or DC sources, or a battery source for portability of system 10. Switch 23 is disposed at any convenient location on housing 17 for interconnection of light source 19 and power source 22 for activation of light source 19.

Detector portion 12 comprises a second substantially light tight housing 26 enclosing optical detector (photodetector) 25. Detector 25 may comprise a photodiode, phototransistor, selenium cell or photoresistor, or other detector type as would occur to the skilled artisan guided by these teachings.

Power source 27 comprises any suitable power source in the form of AC, DC or battery power (for portability). Switch 28 :interconnects detector 25 and power source 27 for selective activation of detector 25.

In the operation of system 10, light source portion 11 is placed on the side of transparency having the crazed condition and detector portion 12 is placed on the side of transparency 13 opposite source portion 11 and in registering relationship therewith. Light source portion 11 and detector portion 12 are placed relative to each other such that light from source 19 may be projected through transparency 13 into housing 26. Light baffle 30 is disposed in any suitable position within either or both of housings 17,26 in order to prevent light from source 19 from direct projection onto detector 25. Light rays 31 from source 19 are projected onto region 14 and are partially reflected as rays 31r from any crazing condition 14 in the form of microcracks 15 present in transparency 13. Because microcracks 15 tend to be approximately perpendicular to the surface of transparency 13, reflected rays 31r are concentrated in the area of lens 32 and imaged onto photodetector 33 of detector 25. The light detected by detector 25 is proportional to the degree of crazing present in transparency 13 and may be displayed using any suitable display means such as digital display 34. System 10 may be calibrated using a piece of translucent plastic having no crazing but which scatters a known percentage of light toward detector 25. Alternative calibration methods may be envisioned by the skilled artisan practicing the invention, the same not being limiting of the invention, and may include use of a known diffuser. Calibration of system 10 may be achieved by rotating detector portion 12 through 180° from the normal measurement orientation and placing it in registration with portion 11 with no transparency therebetween, which provides a measure related to luminance of source 19 and sensitivity of detector 25.

In order for system 10 to be suitably portable, handles 35,36 may be attached to portions 11,12 substantially as shown so that portions 11,12 may be hand held. Each of housings 17,26 are preferably lined with a dark, light absorbing material to prevent reading errors resulting from light reflection or scatter from the interior surfaces of the housings. Because the structure of aircraft windows may include two or more transparencies in a spaced relationship, crazing measurements in situ on an aircraft window using system 10 may require a different spacing between source 19 and detector 25 than corresponding measurements on a single transparency (for example, in a laboratory environment). Accordingly, movable sleeve 37 may be included in either housing 11 or 12 in order to permit selective expansion of the spacing between source 19 and detector 25. If system 10 is to be used in sunlight or other lighted environment, optional flexible skirts 38,39 may be disposed on each respective periphery of housing 17,26 (or sleeve 37) for contacting transparency 13 to prevent ambient light from entering housing 26 and affecting light intensity readings on detector 25.

In the measurement of example transparencies in demonstration of the invention, three aircraft passenger windows having light, medium, and heavy crazing were measured and compared to measurements on a new clear piece of plastic and a dirty scratched piece of plastic, neither of which were crazed. Test results were repeatable within 10% and accurately separated the different levels of crazing correctly as well as being insensitive to the non-crazed plastic transparencies.

In an alternative embodiment of the invention, system 10 may include a second light source and detector disposed within respective housings 17,26 at 90° from source 19 and detector 25 to provide increased sensitivity to multiple orientations of microcracks 15.

Referring now to FIG. 3, shown therein is a schematic perspective view in partial cutaway of an alternative embodiment of the invention, in the form of system 40, wherein a plurality of light sources 41 are disposed in a generally circular arrangement behind annular light baffle 42 within housing 43, and a corresponding plurality of detectors 45 are disposed in a generally circular arrangement within housing 46 for placement in registering relationship on opposite sides of a transparency to be measured for crazing. It is noted that although four sources 41 and four corresponding detectors 45 are shown in quadrature within housings 43,46, any suitable plurality of sources and detectors may be used within the intended scope of these teachings and the appended claims, the specific plurality not considered limiting of the invention. A sequencing circuit 50 interconnects light sources 41 and power supply 52 therefor with correspondingly placed detectors 45 and power supply 53 therefor such that only one light source 41 and the correspondingly placed detector 45 are activated at a time, and the plurality of sources 41 and detectors 45 may be activated sequentially in pairs. The plurality of sources 41 and detectors 45 within system 40 allows measurement of crazing in a transparency with respect to substantially all orientations of microcracks 55 in the transparency without manually repositioning housings 43,46 between measurement events.

The invention therefore provides system and method for in situ measurement of crazing in a transparency utilizing one or more diffuse distributed light sources and a corresponding number of suitably placed detectors. It is understood that modifications to the invention may be made as might occur to one with skill in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

I claim:

1. A system for measuring crazing in a transparency, comprising:

(a) a first substantially light tight housing having an open end for placement near a first side of a transparency at the portion thereof having a crazed condition;

(b) a light source disposed within said first housing for projecting light through said transparency at said portion thereof having a crazed condition;

(c) a second substantially light tight housing having an open end for placement in registration with said first housing near the second side of said transparency opposite said first housing;

(d) an optical detector within said second housing and positioned therein to detect only fight from said source reflected from said portion of said transparency having said crazed condition;

(e) baffle means within one or both of said first and second housings for blocking direct; projection of light from said source to said detector; and (f) a source of power for said source and said optical detector.

2. The system of claim 1 wherein said optical detector includes a photodiode, phototransistor, selenium cell or photoresistor.

3. The system of claim 1 further comprising a flexible skirt around the periphery of each of said housings for placement against said transparency to prevent ambient light from entering said housings.

4. The system of claim 2 further comprising a light diffuser disposed between said source and said open end of said first housing.

5. A method for measuring crazing in a transparency, comprising the steps of:

(a) providing a substantially diffuse light source for placement near a first side of a transparency;

(b) providing an optical detector for placement near the second side of said transparency opposite said first housing;

(c) providing means for excluding ambient light from said detector;

(d) projecting light from said light source through said transparency at the portion thereof having a crazed condition;

(e) blocking direct projection of light from said source to said detector; and (f) detecting the amount of light from said source which is reflected from said portion of said transparency having said crazed condition.

6. A system for measuring crazing in a transparency, comprising:

(a) a first substantially light fight housing having an open end for placement near a first side of a transparency;

(b) a plurality of light sources disposed in a generally circular arrangement within said first housing for projecting light through said transparency at the portion thereof having a crazed condition;

(c) a second substantially light fight housing having an open end for placement in registration with said first housing near the second side of said transparency opposite said first housing;

(d) a plurality of optical detectors corresponding in number with said plurality of light sources, said optical detectors disposed within said second housing in a generally circular arrangement, each said detector selectively positioned within said second housing opposite a corresponding said light source;

(e) means defining a light baffle within one or both of said first and second housings for blocking the direct projection of light from a said source to the corresponding said detector;

(f) a source of power for said sources and said detectors; and (g) means for selectively activating a selected source and corresponding detector.

7. The system of claim 6 wherein each of said optical detectors includes a photodiode, phototransistor, selenium cell or photoresistor.

8. The system of claim 6 further comprising a flexible skin around the periphery of each of said housings for placement against said transparency to prevent ambient light from entering said housings.

* * * * *